United States Patent
Bierman et al.

(10) Patent No.: US 9,895,514 B2
(45) Date of Patent: Feb. 20, 2018

(54) MEDICAL DEVICE SECUREMENT SYSTEM AND METHOD

(71) Applicant: MADDOC MEDICAL PRODUCTS, INC., Los Angeles, CA (US)

(72) Inventors: Steven Bierman, Del Mar, CA (US); Tu Nguyen, Escondido, CA (US)

(73) Assignee: Maddoc Medical Products, Inc., Los Angeles, CA (US)

( * ) Notice: Subject to any disclaimer, the term of this patent is extended or adjusted under 35 U.S.C. 154(b) by 0 days.

(21) Appl. No.: 14/639,888

(22) Filed: Mar. 5, 2015

(65) Prior Publication Data
US 2015/0209552 A1     Jul. 30, 2015

Related U.S. Application Data

(63) Continuation-in-part of application No. 14/607,063, filed on Jan. 27, 2015.
(Continued)

(51) Int. Cl.
| | |
|---|---|
| *A61M 25/02* | (2006.01) |
| *A61M 39/10* | (2006.01) |
| *A61M 5/158* | (2006.01) |

(52) U.S. Cl.
CPC .......... *A61M 25/02* (2013.01); *A61M 5/158* (2013.01); *A61M 39/10* (2013.01); *A61M 2005/1586* (2013.01); *A61M 2025/0246* (2013.01)

(58) Field of Classification Search
CPC ............ A61M 25/02; A61M 2025/024; A61M 2025/0266; A61M 2025/028;
(Continued)

(56) References Cited

U.S. PATENT DOCUMENTS

| 2,525,398 A | 10/1950 | Collins |
| 2,533,961 A | 12/1950 | Rousseau et al. |

(Continued)

FOREIGN PATENT DOCUMENTS

| CA | 995995 A1 | 8/1976 |
| CA | 2281457 A1 | 8/1999 |

(Continued)

OTHER PUBLICATIONS

Photograph of Bard Securis Stabilization Device and Instructions for Use.

*Primary Examiner* — Bhisma Mehta
*Assistant Examiner* — Brandy S Lee
(74) *Attorney, Agent, or Firm* — Klein, O'Neill & Singh, LLP

(57) ABSTRACT

A medical device securement system is configured to secure medical devices such as catheters in place. The securement system includes an anchor pad that attaches to a patient's skin. A malleable support base is attached to an upper surface of the anchor pad. The support base has front and back inclined surfaces that are separated by an offset surface that extends generally normal to both of the inclined surfaces. A spot of adhesive is applied to one or more of the inclined surfaces. A catheter assembly includes a connector having a first connector portion with a diameter larger than an adjacent second structure. The catheter assembly is attached to the support base with the first connector portion engaged with and supported by the back inclined surface, and the second connector portion engaged with and supported by the front inclined surface.

25 Claims, 8 Drawing Sheets

Related U.S. Application Data

(60) Provisional application No. 62/083,015, filed on Nov. 21, 2014, provisional application No. 61/932,093, filed on Jan. 27, 2014.

(58) Field of Classification Search
CPC .... A61M 2025/026; A61M 2025/0273; A61M 2005/1416; A61M 2025/0246; A61M 2025/0253; A61M 5/1415; A61M 5/1418; A61M 2005/1586; A61M 39/10; A61M 5/158

See application file for complete search history.

(56) References Cited

U.S. PATENT DOCUMENTS

| | | |
|---|---|---|
| 2,707,953 A | 5/1955 | Ryan |
| 3,059,645 A | 10/1962 | Hasbrouck et al. |
| 3,064,648 A | 11/1962 | Bujan |
| 3,167,072 A | 1/1965 | Stone et al. |
| 3,482,569 A | 12/1969 | Raffaelli, Sr. |
| 3,529,597 A | 9/1970 | Fuzak |
| 3,602,227 A | 8/1971 | Andrew |
| 3,613,663 A | 10/1971 | Johnson |
| 3,630,195 A | 12/1971 | Santomieri |
| 3,677,250 A | 7/1972 | Thomas |
| 3,766,915 A | 10/1973 | Rychlik |
| 3,834,380 A | 9/1974 | Boyd |
| 3,847,370 A | 11/1974 | Engelsher |
| 3,856,020 A | 12/1974 | Kovac |
| 3,896,527 A | 7/1975 | Miller et al. |
| 3,900,026 A | 8/1975 | Wagner |
| 3,906,946 A | 9/1975 | Nordström |
| 3,942,228 A | 3/1976 | Buckman et al. |
| 3,973,565 A | 8/1976 | Steer |
| 4,020,835 A | 5/1977 | Nordström et al. |
| 4,057,066 A | 11/1977 | Taylor |
| 4,059,105 A | 11/1977 | Cutruzzula et al. |
| 4,082,094 A | 4/1978 | Dailey |
| 4,114,618 A | 9/1978 | Vargas |
| 4,129,128 A | 12/1978 | McFarlane |
| 4,133,307 A | 1/1979 | Ness |
| 4,142,527 A | 3/1979 | Garcia |
| 4,161,177 A | 7/1979 | Fuchs |
| 4,165,748 A | 8/1979 | Johnson |
| 4,193,174 A | 3/1980 | Stephens |
| 4,224,937 A | 9/1980 | Gordon |
| 4,248,229 A | 2/1981 | Miller |
| 4,250,880 A | 2/1981 | Gordon |
| 4,275,721 A | 6/1981 | Olson |
| 4,316,461 A | 2/1982 | Marais et al. |
| 4,324,236 A | 4/1982 | Gordon et al. |
| 4,326,519 A | 4/1982 | D'Alo et al. |
| 4,333,468 A | 6/1982 | Geist |
| 4,362,156 A | 12/1982 | Feller, Jr. et al. |
| 4,392,853 A | 7/1983 | Muto |
| 4,397,647 A | 8/1983 | Gordon |
| 4,405,312 A | 9/1983 | Gross et al. |
| 4,449,975 A | 5/1984 | Perry |
| 4,453,933 A | 6/1984 | Speaker |
| 4,474,559 A | 10/1984 | Steiger |
| 4,480,639 A | 11/1984 | Peterson et al. |
| 4,516,968 A | 5/1985 | Marshall et al. |
| 4,517,971 A | 5/1985 | Sorbonne |
| 4,563,177 A | 1/1986 | Kamen |
| 4,627,842 A | 12/1986 | Katz |
| 4,633,863 A | 1/1987 | Filips et al. |
| 4,650,473 A | 3/1987 | Bartholomew et al. |
| 4,660,555 A | 4/1987 | Payton |
| 4,711,636 A | 12/1987 | Bierman |
| 4,737,143 A | 4/1988 | Russell |
| 4,742,824 A | 5/1988 | Payton et al. |
| 4,762,513 A | 8/1988 | Choy et al. |
| 4,808,162 A | 2/1989 | Oliver |
| 4,822,342 A | 4/1989 | Brawner |
| 4,823,789 A | 4/1989 | Beisang, III |
| 4,826,486 A | 5/1989 | Palsrok et al. |
| 4,846,807 A | 7/1989 | Safadago |
| 4,852,844 A | 8/1989 | Villaveces |
| 4,857,058 A | 8/1989 | Payton |
| 4,863,432 A | 9/1989 | Kvalo |
| 4,869,465 A | 9/1989 | Yirmiyahu et al. |
| 4,880,412 A | 11/1989 | Weiss |
| 4,896,465 A | 1/1990 | Rhodes et al. |
| 4,897,082 A | 1/1990 | Erskine |
| 4,898,587 A | 2/1990 | Mera |
| 4,919,654 A | 4/1990 | Kalt |
| 4,921,199 A | 5/1990 | Villaveces |
| 4,932,943 A | 6/1990 | Nowak |
| 4,944,728 A | 7/1990 | Carrell et al. |
| 4,952,207 A | 8/1990 | Lemieux |
| 4,955,864 A | 9/1990 | Hajduch |
| 4,976,700 A | 12/1990 | Tollini |
| 4,981,475 A | 1/1991 | Haindl |
| 4,997,421 A | 3/1991 | Palsrok et al. |
| 5,000,741 A | 3/1991 | Kalt |
| 5,037,397 A | 8/1991 | Kalt et al. |
| 5,073,166 A | 12/1991 | Parks et al. |
| 5,073,170 A | 12/1991 | Schneider |
| 5,084,026 A | 1/1992 | Shapiro |
| 5,098,399 A | 3/1992 | Tollini |
| 5,112,313 A | 5/1992 | Sallee |
| 5,137,519 A | 8/1992 | Littrell et al. |
| 5,147,322 A | 9/1992 | Bowen et al. |
| 5,156,641 A | 10/1992 | White |
| 5,192,273 A | 3/1993 | Bierman et al. |
| 5,192,274 A | 3/1993 | Bierman |
| 5,195,981 A | 3/1993 | Johnson |
| 5,226,892 A | 7/1993 | Boswell |
| 5,236,421 A | 8/1993 | Becher |
| 5,266,401 A | 11/1993 | Tollini |
| 5,267,967 A | 12/1993 | Schneider |
| 5,282,463 A | 2/1994 | Hammersley |
| 5,292,312 A | 3/1994 | Delk et al. |
| 5,304,146 A | 4/1994 | Johnson et al. |
| 5,306,243 A | 4/1994 | Bonaldo |
| 5,314,411 A | 5/1994 | Bierman et al. |
| 5,338,308 A | 8/1994 | Wilk |
| 5,342,317 A | 8/1994 | Claywell |
| 5,344,406 A | 9/1994 | Spooner |
| 5,344,414 A | 9/1994 | Lopez et al. |
| 5,346,479 A | 9/1994 | Schneider |
| 5,352,211 A | 10/1994 | Merskelly |
| 5,354,282 A | 10/1994 | Bierman |
| 5,354,283 A | 10/1994 | Bark et al. |
| 5,372,589 A | 12/1994 | Davis |
| 5,380,293 A | 1/1995 | Grant |
| 5,380,294 A | 1/1995 | Persson |
| 5,380,301 A | 1/1995 | Prichard et al. |
| 5,380,395 A | 1/1995 | Uchida |
| 5,382,239 A | 1/1995 | Orr et al. |
| 5,382,240 A | 1/1995 | Lam |
| 5,389,082 A | 2/1995 | Baugues et al. |
| 5,395,344 A | 3/1995 | Beisang, III et al. |
| 5,403,285 A | 4/1995 | Roberts |
| 5,413,562 A | 5/1995 | Swauger |
| 5,443,460 A | 8/1995 | Miklusek |
| 5,449,349 A | 9/1995 | Sallee et al. |
| 5,456,671 A | 10/1995 | Bierman |
| 5,468,228 A | 11/1995 | Gebert |
| 5,468,230 A | 11/1995 | Corn |
| 5,468,231 A | 11/1995 | Newman et al. |
| 5,470,321 A | 11/1995 | Forster et al. |
| D364,922 S | 12/1995 | Bierman |
| 5,484,420 A | 1/1996 | Russo |
| 5,496,282 A | 3/1996 | Militzer et al. |
| 5,496,283 A | 3/1996 | Alexander |
| 5,499,976 A | 3/1996 | Dalton |
| 5,520,656 A | 5/1996 | Byrd |
| 5,522,803 A | 6/1996 | Teissen-Simony |
| 5,527,293 A | 6/1996 | Zamierowski |
| 5,531,695 A | 7/1996 | Swisher |
| 5,549,567 A | 8/1996 | Wolman |
| D375,355 S | 11/1996 | Bierman |
| 5,578,013 A | 11/1996 | Bierman |

(56) References Cited

U.S. PATENT DOCUMENTS

| | | | |
|---|---|---|---|
| 5,593,395 A | 1/1997 | Martz | |
| 5,685,859 A | 11/1997 | Kornerup | |
| 5,693,032 A | 12/1997 | Bierman | |
| 5,697,907 A | 12/1997 | Gaba | |
| 5,722,959 A | 3/1998 | Bierman | |
| 5,738,660 A | 4/1998 | Luther | |
| 5,795,335 A | 8/1998 | Zinreich | |
| 5,810,781 A | 9/1998 | Bierman | |
| 5,855,591 A * | 1/1999 | Bierman | A61M 25/02 24/16 PB |
| 5,911,707 A | 6/1999 | Wolvek et al. | |
| 6,001,081 A | 12/1999 | Collen | |
| 6,027,480 A | 2/2000 | Davis et al. | |
| 6,132,398 A | 10/2000 | Bierman | |
| 6,213,979 B1 | 4/2001 | Bierman | |
| 6,224,571 B1 * | 5/2001 | Bierman | A61M 25/02 604/174 |
| 6,332,874 B1 | 12/2001 | Eliasen et al. | |
| 6,428,516 B1 | 8/2002 | Bierman | |
| 6,585,703 B1 | 7/2003 | Kassel et al. | |
| 6,689,104 B2 | 2/2004 | Bierman | |
| 6,786,892 B2 * | 9/2004 | Bierman | A61M 25/02 128/DIG. 26 |
| 6,872,194 B2 | 3/2005 | Doyle et al. | |
| 6,984,145 B1 | 1/2006 | Lim | |
| 7,153,291 B2 | 12/2006 | Bierman | |
| 7,651,479 B2 | 1/2010 | Bierman | |
| 7,811,258 B2 | 10/2010 | Bierman | |
| 8,146,210 B2 | 4/2012 | Nishtala | |
| 8,241,253 B2 | 8/2012 | Bracken | |
| 8,394,067 B2 | 3/2013 | Bracken et al. | |
| 8,486,004 B1 * | 7/2013 | Propp | A61M 25/02 604/178 |
| 8,500,698 B2 | 8/2013 | Kyvik et al. | |
| 8,506,531 B2 | 8/2013 | Bierman | |
| 8,540,680 B2 | 9/2013 | Burn | |
| 8,556,859 B2 | 10/2013 | Nilson et al. | |
| 8,608,704 B2 | 12/2013 | Bierman | |
| 8,608,705 B2 | 12/2013 | Peters et al. | |
| 8,679,066 B2 | 3/2014 | Aviles | |
| 8,734,400 B2 | 5/2014 | Ciccone | |
| 8,740,852 B2 | 6/2014 | Aviles | |
| 8,834,425 B2 | 9/2014 | Bracken et al. | |
| 8,881,899 B2 | 11/2014 | Fink et al. | |
| 8,900,196 B2 | 12/2014 | Andino | |
| 8,926,565 B2 | 1/2015 | Cusworth | |
| 2006/0247577 A1 * | 11/2006 | Wright | A61M 5/158 604/174 |
| 2011/0319830 A1 * | 12/2011 | Peters | A61M 25/02 604/180 |
| 2013/0204190 A1 * | 8/2013 | Wilborn | A61M 25/02 604/180 |
| 2015/0157845 A1 * | 6/2015 | Bayly | A61M 39/10 285/33 |

FOREIGN PATENT DOCUMENTS

| | | |
|---|---|---|
| EP | 0064284 A2 | 4/1982 |
| EP | 0247590 A2 | 12/1987 |
| EP | 0356683 A1 | 3/1990 |
| FR | 1184139 | 7/1959 |
| GB | 2063679 A | 6/1981 |
| GB | 2086466 A | 5/1982 |
| GB | 2211417 A | 7/1989 |
| JP | 02-093530 | 4/1990 |
| JP | 04-051567 | 2/1992 |
| JP | 06-344852 | 12/1994 |
| JP | 07-028563 | 1/1995 |
| WO | WO 80/01458 | 7/1980 |
| WO | WO 85/02774 | 7/1985 |
| WO | WO 90/04991 | 5/1990 |
| WO | WO 91/16939 | 11/1991 |
| WO | WO 92/19309 | 11/1992 |
| WO | WO 96/10435 | 4/1996 |
| WO | WO 97/15342 | 5/1997 |

* cited by examiner

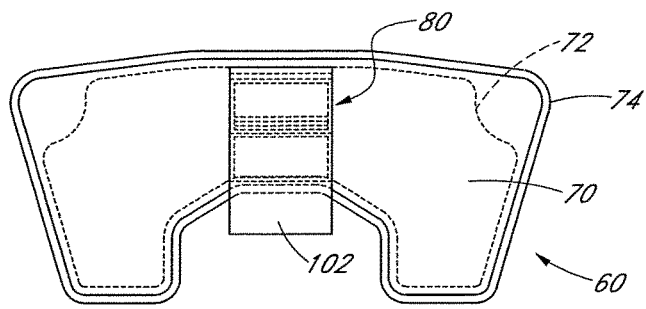
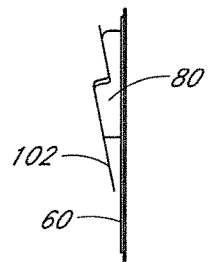
FIG. 4A  FIG. 4B
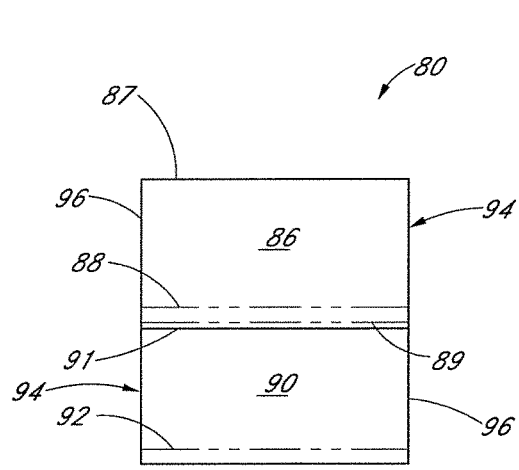
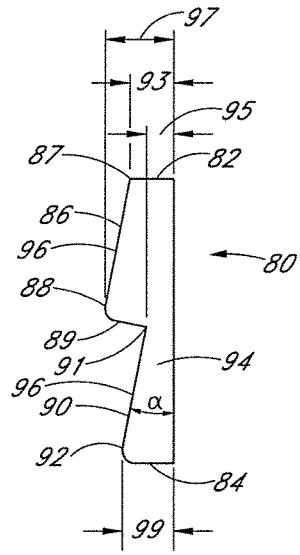
FIG. 5A  FIG. 5B
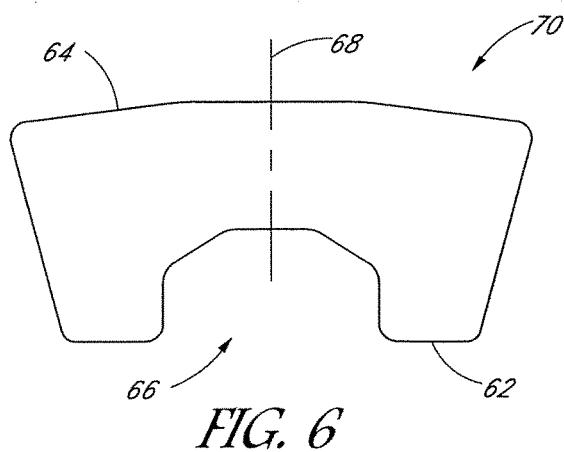
FIG. 6

MEDICAL DEVICE SECUREMENT SYSTEM AND METHOD

CROSS-REFERENCE TO RELATED APPLICATIONS

This application claims priority to U.S. Provisional Application Nos. 62/083,015, filed Nov. 21, 2014 and 61/932,093, filed Jan. 27, 2014. This application also claims priority as a continuation-in-part of U.S. application Ser. No. 14/607,063, which was filed Jan. 27, 2015. The entirety of each of these priority applications is hereby incorporated by reference.

BACKGROUND

The present disclosure relates to the field of securement systems for attaching a medical device to a patient.

Medical treatments often involve relatively long term use of tubes such as catheters to deliver fluids to or from a patient. For example, percutaneously inserted catheters are often used to deliver fluids directly into the bloodstream. In such cases, the catheter extends through the patient's skin and tissues and into a blood vessel. Once the catheter is placed within the patient, it is desired to prevent unintentional migration or dislodgment of the catheter. As such, the catheter and/or a catheter hub to which it is attached are typically affixed to the patient by surgical tape and/or a securement device.

Prior securement methods and devices suffer from various shortfalls. For example, surgical tape can provide an insecure fit, and the tape can present an increased risk of spreading infection. However, specialized catheter securement devices can be excessively bulky, uncomfortable for patients, and expensive. Further, some securement devices can only be operated with specially-made catheter assemblies.

SUMMARY

There is a need in the art for a medical device securement system that securely holds the catheter assembly so as to resist migration and dislodgment, is comfortable for the patient, is compatible with standard catheter assemblies, and is neither unduly bulky nor expensive.

In accordance with one embodiment, the present specification describes a medical article securement device having an anchor pad and a malleable, compressible support base. The anchor pad is configured to be adhered to skin of a patient. The support base is attached to and extends upwardly from the anchor pad. The support base has a first inclined upper surface and a second inclined upper surface that are longitudinally aligned with one another. An offset surface extends between the first and second inclined upper surfaces, which are planar and parallel to one another. A medical article has a first connector portion having a first diameter and a second connector portion having a second diameter. The second connector portion is positioned adjacent a distal end of the first connector portion, and the second diameter is less than the first diameter. The first connector portion is supported by the second inclined upper surface and the second connector portion is supported by the first inclined upper surface.

In accordance with another embodiment, a portion of the distal end of the first connector portion engages the offset surface. Another such embodiment additionally comprises an adhesive layer disposed on a portion of the second inclined upper surface, and the second connector is adhered to the second inclined upper surface via the adhesive layer.

Yet another embodiment additionally comprises a suture attached to the support pad and wrapped about one of the first and second connector portions.

In yet another embodiment, the first inclined upper surface does not have an adhesive layer attached thereto.

In still another embodiment, the adhesive layer is disposed on only a portion of the second inclined upper surface.

In a yet further embodiment, the adhesive layer is configured to preferentially stick to the second inclined upper surface rather than the second connector portion.

In a still further embodiment, the support base comprises a foam.

In still another embodiment, the support base is a monolithic piece of foam. In other embodiments, however, the support base comprises a first portion constructed of a first material and a second portion constructed of a second material, and the first material is more malleable than the second material.

In accordance with another embodiment, the present specification provides a method, comprising applying an anchor pad of a securement device onto the skin of a patient, wherein the anchor pad has a support base extending therefrom, and the support base has a first inclined surface and a second inclined surface, the first and second inclined surfaces being parallel and joined end to end by an offset surface. A medical device connector system is rested on the support base so that a first connector portion is supported by the second inclined surface and a second connector portion is supported by the first inclined surface. A distal end of the first connector portion rests against the offset surface. An adhesive cover is adhered onto the medical device connector system.

Some such embodiments additionally comprise attaching the first connector portion to a glue dot arranged on the second inclined surface.

Yet another embodiment additionally comprises detaching the first connector portion from the second connector portion.

Still another embodiment additionally comprises detaching the first connector portion from the second inclined surface.

A yet further embodiment additionally comprises discarding the first connector portion and replacing it with a second first connector portion, and additionally comprises attaching the second first connector portion to the second connector portion and attaching the second first connector portion to the second inclined surface.

BRIEF DESCRIPTION OF THE DRAWINGS

FIG. 4A is a top plan view of the securement device of FIG. 2;

FIG. 4B is a side view of the securement device of FIG. 4A;

FIG. 5A is a top plan view of a support base for use with the securement device of FIG. 2;

FIG. 5B is a side view of the support base of FIG. 5A;

FIG. 6 is a top plan view of an anchor pad of the securement device of FIG. 2;

DESCRIPTION

The following description and the accompanying figures describe and show embodiments that serve as illustrative examples of medical device securement systems and associated methods, including various inventive aspects and features. The illustrated embodiments are made in connection with a catheter assembly. Illustration of the securement system in this context is not intended to limit the disclosed aspects and features to the specific embodiments or to imply that such aspects and features can be used only with the illustrated catheter assembly. Those of skill in the art will recognize that the disclosed aspects and features are not limited to any particular embodiment of a securement system, and securement systems that include one or more of the inventive aspects and features described herein can be used in connection with a variety of medical articles.

Figure 1:
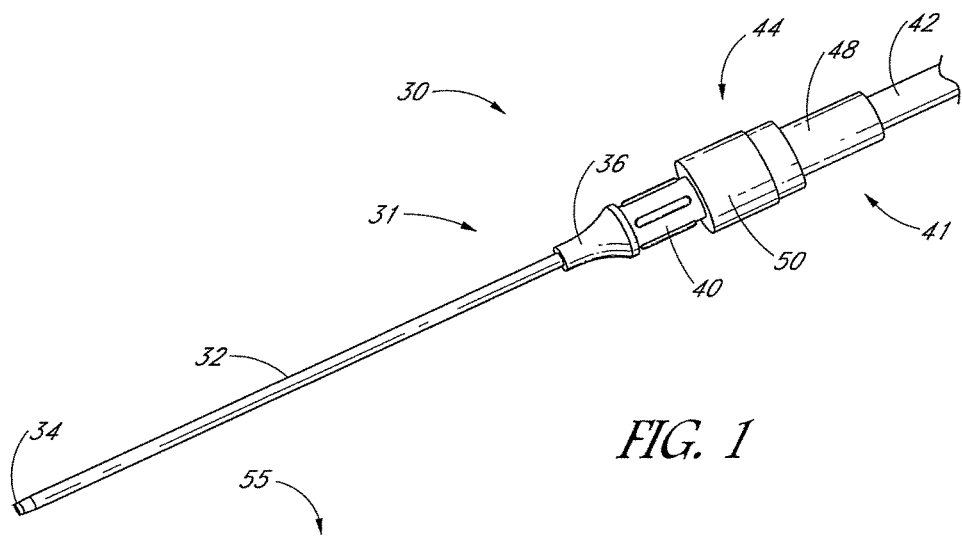
FIG. 1 shows a perspective view of a catheter assembly in accordance with the present disclosure.
Figure 2:
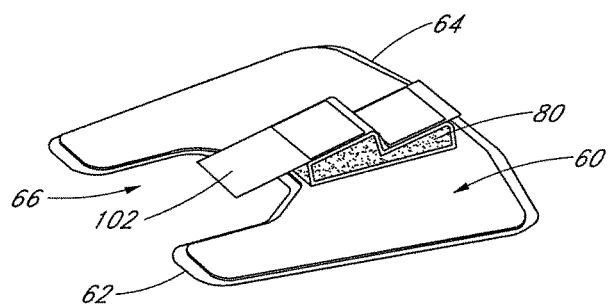
FIG. 2 is a perspective view of a securement device in accordance with the present disclosure.

With initial reference to FIG. 1, a catheter assembly 30 is shown. The illustrated catheter assembly 30 includes a catheter 31 comprising an elongated catheter tube 32 that terminates in a tapered distal tip 34. A proximal end of the catheter tube 32 is attached to a bushing 36, which in turn is attached to a catheter hub 40. The illustrated catheter tube 32 preferably is flexible and configured for use in a standard venipuncture procedure to provide access to a patient's blood vessel. A proximal end of the catheter hub 40 preferably is threaded. In the illustrated embodiment, a fluid delivery line 41 comprises medical tubing such as intravenous (IV) tubing 42 having a connector such as a Luer connector 44. The IV tubing 42 attaches to an elongated fitting 48 which fits into a proximal end of the catheter hub 40. A collar or spin nut 50 slides over the elongated fitting 48 and has internal threads that can engage the hub's proximal threads so as to attach the fluid delivery line 41 to the catheter 31.

With reference next to FIGS. 2-6, a catheter securement device 55 is configured to hold the catheter assembly 30 in place on a patient. The securement device 55 comprises an anchor pad 60 having a front edge 52 and a back edge 64. The front edge 62 includes a cavity 66. An axis 68 extends centrally from the front to the back of the anchor pad 60. The anchor pad 60 is configured to engage the patient's skin and hold the securement device 55 on the skin. As such, depending on the location of placement on the patient and the specific goals of the device, the shape of the anchor pad 60 may vary in different embodiments.

The anchor pad 60 preferably has a laminate structure with an upper layer 70 and a lower adhesive layer 72. In one preferred embodiment, the upper layer 70 comprises a woven polyester material commercially available from Tyco under the name "Tricot." It is to be understood, however, that other embodiments may employ woven or nonwoven polymer or non-polymer textile materials. In yet further embodiments the upper layer may be constructed of paper or foam.

The lower adhesive layer 72 is configured to adhere the anchor pad 60 to the skin of the patient, and can include a medical grade adhesive that is either diaphoretic or non-diaphoretic, depending upon the particular application. In some embodiments the lower adhesive layer 72 may include additional types of medical adhesives. Also, some embodiments of the lower adhesive layer 72 may comprise anti-bacterial or anti-microbial material such as a legal dynamic metal salts or oxides, or combinations thereof. The adhesive layer 72 may be a solid layer or may be configured as an intermittent layer such as in the pattern of spots or strips.

A removable release liner 74 preferably covers the adhesive layer 72 before use. The release liner 74 may be configured as a single piece, or may be divided into two or more adjacent pieces in order to may make removal easier. The release liner 74 can be made of any of several materials, including paper, polymers, or combinations thereof. In one embodiment, the release liner 74 may comprise a material made of poly coated, siliconized paper, or another suitable material such as high density polyethylene, polypropylene, polyolefin, or silicon coated paper.

A catheter support base 80 is attached to the upper layer 70 of the anchor pad 60. The support base 80 preferably comprises a malleable, compressible material such as a polyethylene foam or any of several other compressible foams. As shown, preferably the support base 80 is attached to the upper layer 70 so that a front wall 82 of the support base 80 is adjacent the front edge 62 of the anchor pad 60 in the cavity 66, and a back wall 84 of the support base 80 is positioned adjacent the back edge 64 of the anchor pad 60. Preferably the support base 80 is aligned with the axis 68 of the anchor pad 60.

Continuing with reference to FIGS. 2-6, a front inclined surface 86 extends from a front edge 87 at which it intersects the front wall 82 to a back edge 88. An offset surface 89 extends from the front inclined surface back edge 88, preferably at an angle substantially normal to the front inclined surface 86. A back inclined surface 90 extends from a front edge 91 at which it intersects with the offset surface 89 to a back edge 92 at which it intersects the back wall 84. As shown, the front and back inclined surfaces are longitudinally aligned with one another. Opposing side surfaces 94 extend from the front wall 82 to the back wall 84 on opposite sides of the support base 80. The opposing side surfaces 94 intersect the front inclined surface 86 and the back inclined surface 90 along opposing side edges 96.

With particular reference to FIG. 5B, preferably the front and back inclined surfaces 86, 90 are inclined at substantially the same angle α, and the offset surface 89 is substantially normal to both the front and back inclined surfaces 86, 90.

In the illustrated embodiment, a thickness 93 of the support base 80 at the front edge 87 of the front inclined surface 86 is greater than a thickness 95 of the support base at a front edge 91 of the back inclined surface 90, and a thickness 97 of the support base at the back edge 88 of the first inclined surface 86 is greater than a thickness 99 of the back edge 92 of the second inclined surface 90. It is to be understood, however, that in other embodiments these relationships could be reversed or configured otherwise.

Figure 3:
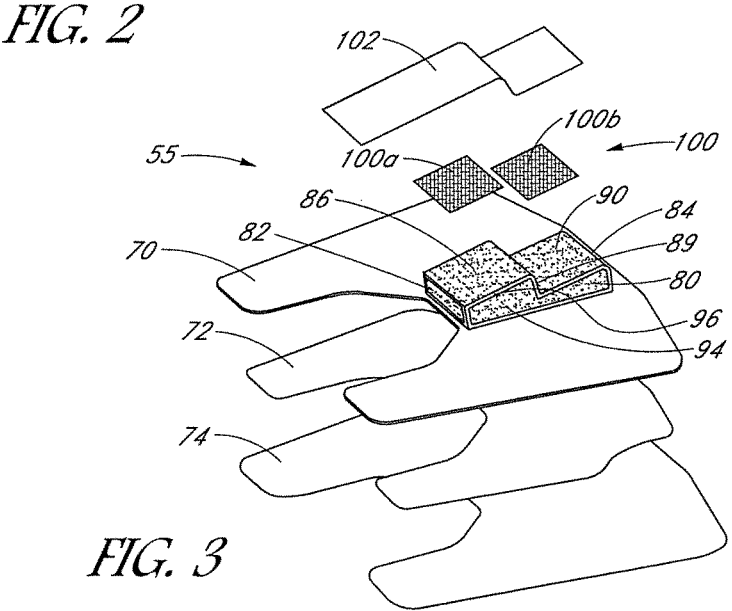
FIG. 3 is an exploded perspective view of the securement device of FIG. 2.

With particular reference next to FIG. 3, an adhesive layer 100 preferably is applied to the support base 80. The adhesive layer 100 can be evenly applied across the front, offset, and back inclined surfaces 86, 89, 90 or can be applied over only a portion of one or more of the surfaces. Adhesive preferably is applied to at least one of the front and back inclined surfaces 86, 90. In the embodiment illustrated in FIG. 3, the adhesive layer 100 comprises a front adhesive portion 100a applied to the front inclined surface 86 and a back adhesive portion 100b applied to the back inclined surface 90. The adhesive portions 100a, 100b shown in FIG. 3 cover substantially all of their respective inclined surfaces 86, 90. It is to be understood that, in other embodiments, adhesive portions may cover only a part of the respective surfaces.

A release liner 102 preferably is applied to the adhesive layer 100. The release liner 102 can be formed from various materials, as is the release liner 74 of the anchor 60, and can have various shapes and sizes. For example in the embodiment illustrated in FIGS. 2-6, the release liner 102 spans the front, offset, and back inclined surfaces 86, 89, 90. In other embodiments, the release liner may be constructed of multiple pieces, and separate pieces of the release liner can contact separate ones of the inclined services. In still further embodiments, adhesive may be applied to only one or the other of the front and back inclined surfaces 86, 90, and the release liner is applied only to the surface bearing adhesive.

Figure 7:
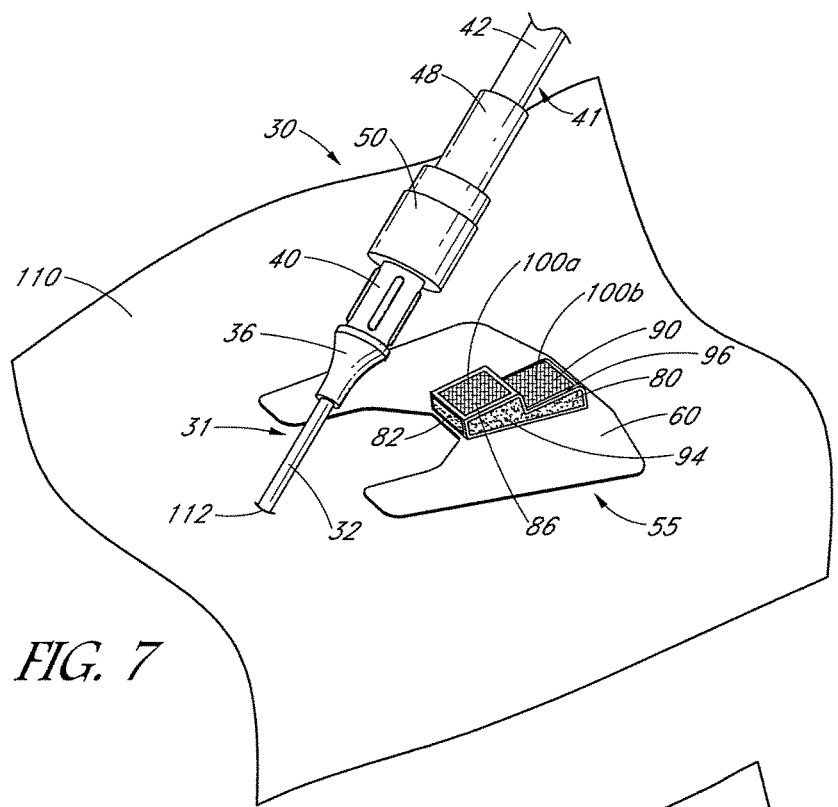
FIG. 7 is a perspective view showing the catheter assembly of FIG. 1 inserted into a patient and the securement device of FIG. 2 affixed to the patient's skin.

As noted above, the anchor pad 60 helps secure a catheter assembly 30 in place on the patient. The clinician may use standard venipuncture procedures to place the catheter tube 32 into a patient's vasculature, and then attach a fluid delivery line 41 to the catheter. FIG. 7 shows such an arrangement in which the catheter tube 32 extends through a patient's skin 110 at an insertion site 112. The clinician can remove the release liner 74 from the anchor pad 60 and place the anchor pad so that its lower adhesive layer 72 engages the patient's skin 110, and its axis 68 is aligned with the insertion site 112. The clinician may also remove the release liner 102 from the support base 80.

Figure 8:
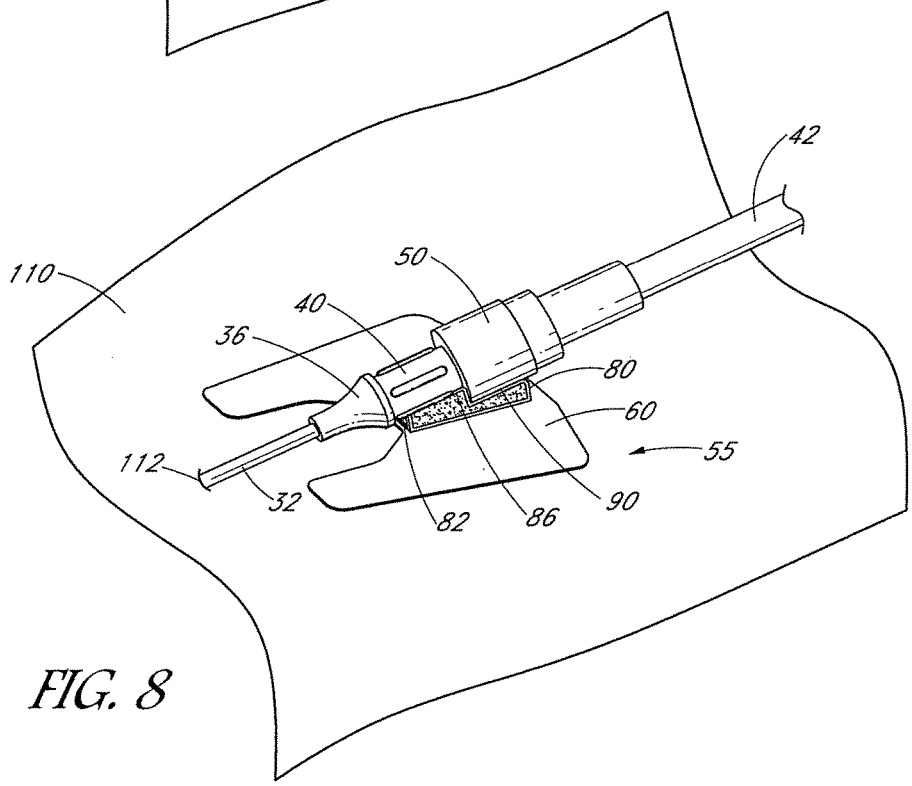
FIG. 8 shows the assembly of FIG. 7 with the catheter assembly attached to the securement device.

With reference next to FIG. 8, the clinician then can place the catheter assembly 30 onto the support base 80 so that the spin nut 50 rests upon the back inclined surface 90 and the catheter hub 40 rests upon the front inclined surface 86. Preferably, the bushing 36, which may have a portion with a diameter greater than the adjacent hub 40, is arranged forwardly of the front wall 82. Due to the thickness 93 at the front edge 87, the bushing 36 is spaced from the patient's skin 110. In the illustrated embodiment, the front adhesive portion 100a engages the hub 40 and the back adhesive portion 100b engages the spin nut 50, holding the catheter assembly 30 in place on the securement member 55. Of course, as discussed above, in another embodiment, only a back portion 100b of adhesive is provided. In still other embodiments, only a front portion 100a of adhesive is provided.

In another embodiment, one or more sutures can be applied to secure the catheter assembly 30 to the support base 80. More specifically, the clinician may suture into the support base rather than suturing into the patient's skin. As such, the suture would secure the catheter assembly to the support base. In some embodiments, such a suture can be applied in addition to adhesive placed on the front or back inclined surfaces. In additional embodiments, no adhesive, or a very weak adhesive, is applied to one or more of the front and back inclined surfaces, and the suture extending through the support base and tied around the catheter assembly secures the catheter assembly to the support base. In still additional embodiments, an adhesive can be applied to one or the other of the front and back inclined surfaces, and a suture can be placed in the other of the front and back inclined surfaces.

In the illustrated embodiment, the offset surface 89 approximates the difference in diameter between the spin nut 50 and the catheter hub 40. As such, the offset surface 89 improves the fit of the catheter assembly 30 on the support pad 80. Further, the offset surface 89 engages a distal end of the spin nut 50, thereby blocking the catheter assembly 30 from moving distally. The adhesive layer 100 provides stable securement of the catheter assembly 30 to the support base 80, and also resists movement of the assembly proximally, or in any direction. The malleable support base 80 accommodates hard portions of the catheter assembly 30, lifting them from the patient's skin 110. Also, deformation of the foam support base 80 absorbs and/or spreads out force is applied by contact points of the catheter assembly 30. As such, the illustrated configuration improves patient comfort.

Figure 9:
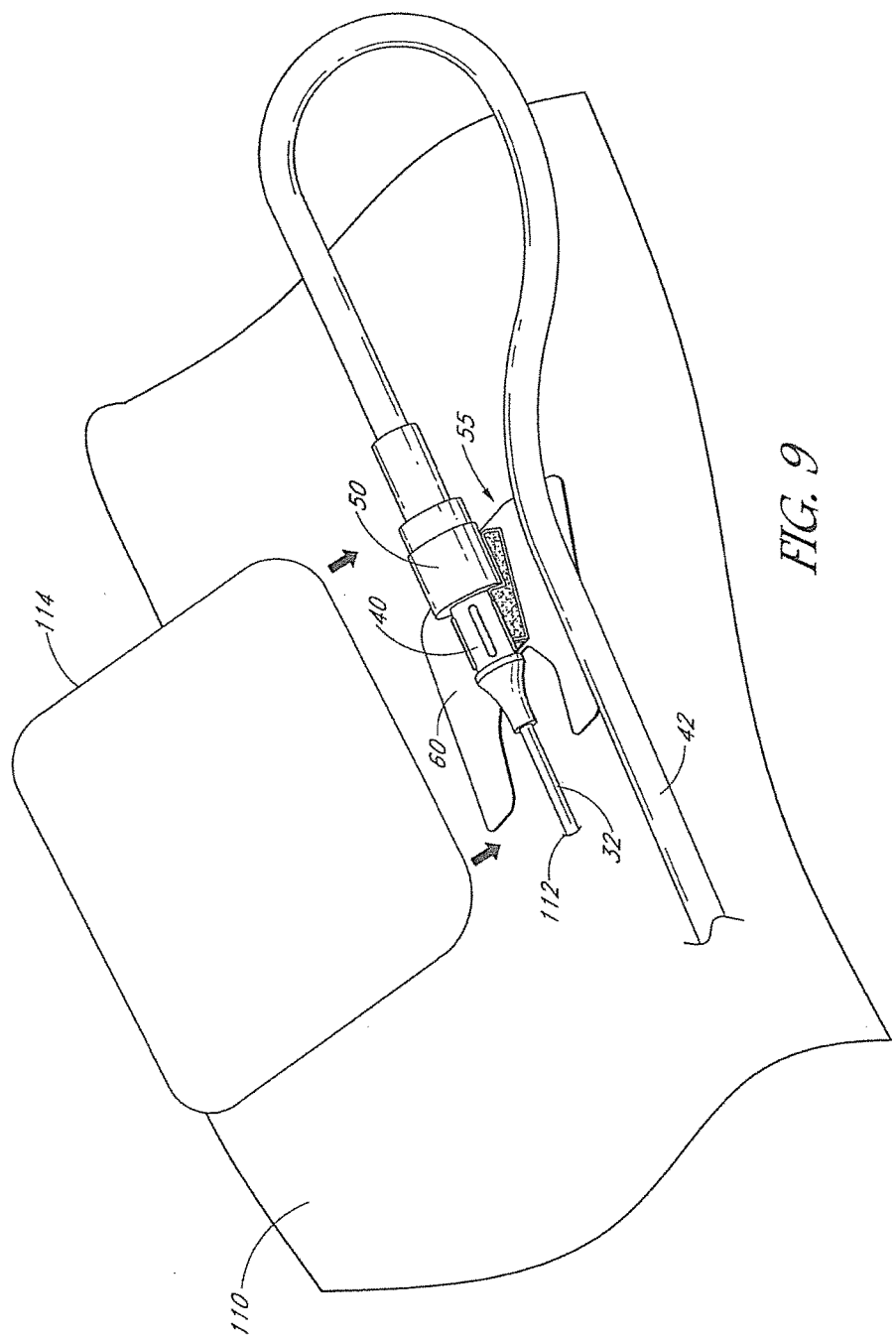
FIG. 9 shows the assembly of FIG. 8 ready for an adhesive cover member to be placed thereon.
Figure 10:
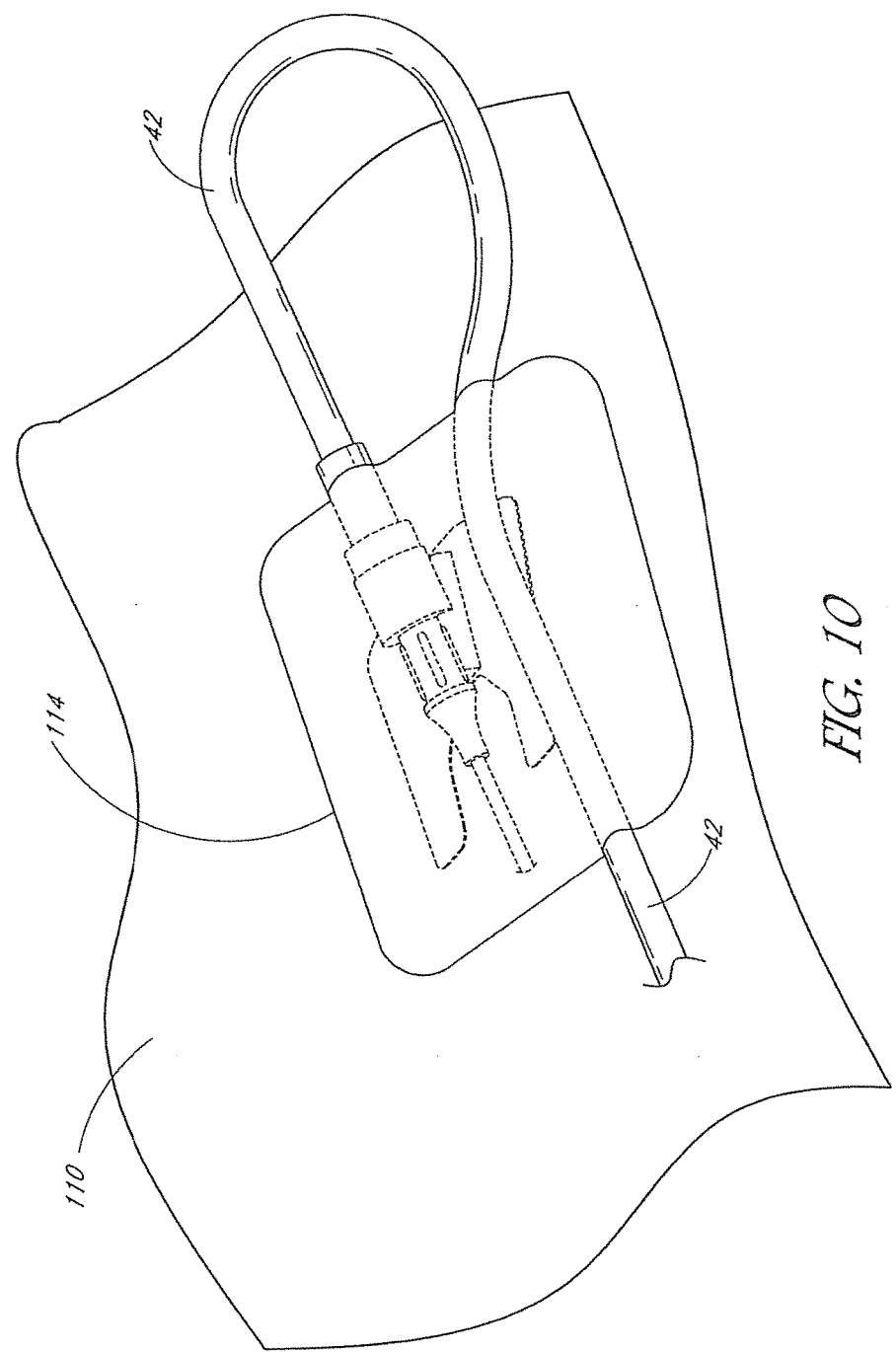
FIG. 10 shows the assembly of FIG. 9 with an adhesive cover member placed there over.

In one embodiment, the adhesive layer 100 may be tacky but not necessarily tacky enough to hold the catheter assembly 30 in place on the securement device 55 without assistance in the long-term. With reference next to FIG. 9, in one embodiment the adhesive layer is tacky enough to hold the catheter assembly in place while the clinician prepares to apply a cover dressing 114, which could be an adhesive-based dressing such as a transparent dressing available from 3M under the brand name Tegaderm™. In this embodiment, the clinician prepares the catheter assembly by forming a loop in the IV tubing 42. The cover dressing 114 is then advanced over the catheter assembly 30, securement device 55, and catheter insertion point 112 as depicted in FIG. 10. In this embodiment, the tacky adhesive layer holds the catheter assembly 30 in place long enough for the adhesive cover dressing 114 to be applied.

In the embodiment illustrated in FIGS. 7-8, the clinician secures the anchor pad 60 to the patient's skin 110 before securing the catheter assembly 30 to the support base 80. In another embodiment, the clinician may adhere the catheter assembly to the support base 80 prior to adhering the anchor pad 60 to the patient's skin 110. In such an embodiment, the catheter assembly 30 can be anchored to the patient's skin 110 without substantially changing the position of the catheter tube 30 relative to the catheter insertion site 112. More specifically, the clinician will not have to adjust the position of the catheter assembly 30 to fit the placement of the securement device 55 on the patient's skin 110.

With continued reference to FIGS. 7 and 8, and additional reference to FIG. 5B, the inclined surfaces 86, 90 preferably are inclined at an angle α selected to position the catheter assembly 30 at a desired incident angle relative to the patient's skin 110. A variety of different angles α can be used, ranging from about 0-45°, and more preferably from about 5-25°. For instance, to secure IV catheters, it is generally desirable to have an angle of incidence of the catheter tube to the skin 110 of between about 7° and 15°, and thus α can also preferably be between about 7° and 15°. For arterial catheters, it is desirable for the angle of incidence of the catheter to the skin to be about 12.5°. Thus, in some embodiments, the incline angle α can be about 12.5°. In the illustrated embodiment, in which an IV catheter is secured by the securement device, the incline angle α is about 11°.

Figure 11:
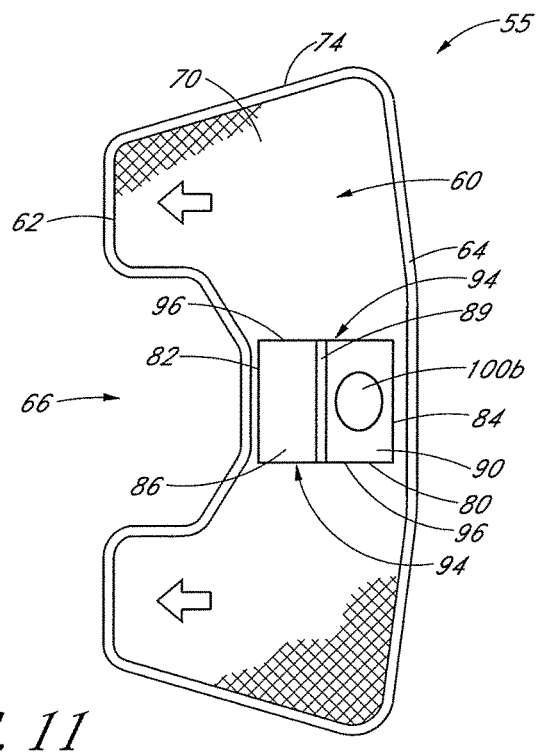
FIG. 11 is a top plan view of another embodiment of a securement device in accordance with the present disclosure.
Figure 13:
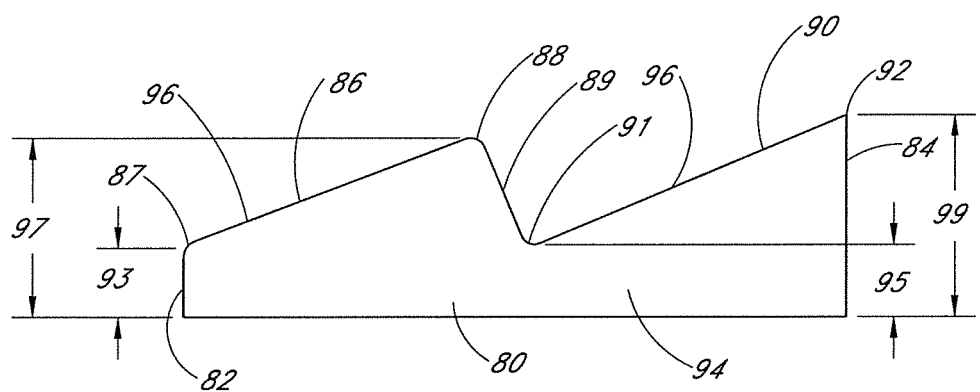
FIG. 13 shows a side view of an embodiment of a support base in accordance with the present disclosure.

With reference next to FIGS. 11 and 13, another embodiment of a securement device 55 also includes an anchor pad 60 upon which a support base 80 is disposed. The illustrated support base 80 preferably is made of an extruded piece of foam that has front and back walls 82, 84. This embodiment is similar to the embodiment described above in connection with FIG. 5B. The illustrated support base 80 includes a front inclined surface 86 and a back inclined surface 90 that are separated by an offset surface 89 in a manner similar to as discussed above. In the illustrated embodiment, the thickness 99 of the support base 80 at the back edge 92 of the back inclined surface 90 is greater than the thickness 97 at the back edge 88 of the front inclined surface 86. However, in the illustrated embodiment, the thickness 93 of the front edge 87 of the front inclined surface 86 is about the same as the thickness 95 of the front edge 91 of the back inclined surface 90.

Continuing with reference to FIG. 13, during manufacture, preferably an elongate foam piece is extruded having the profile of the support base. The elongated foam piece can then be cut into several support bases, which can each then be adhered to the upper surface 70 of an associated anchor pad 60. In the illustrated embodiment, the inclined surfaces 86, 90 are generally planar. In other embodiments, one or both of the inclined surfaces could be curved, such as being concave to curve about an axis of a catheter assembly.

With reference again to FIG. 11, in the illustrated embodiment, adhesive is placed on only a portion of the support base 80. More specifically, as shown, a glue dot is placed generally centrally in the back inclined surface 90, while the front inclined surface 86 and the offset surface 89, are free of adhesive. As shown, the glue dot 100b covers less than two thirds, and in some embodiments about half or less, of the area of the second inclined surface 90. The illustrated glue dot 100b preferably comprises a hot melt adhesive, which is deposited on the second inclined surface 90 during manufacture. A release liner (not shown) can be placed atop the glue dot 100b. Such a release liner need not cover any more than the glue dot 100b, and may not also be disposed over any part of the front inclined surface 86 or the offset surface 89.

It is to be understood, however, that in other embodiments the glue dot can be placed on only the front inclined surface 86. In further embodiments, glue dots can be placed on both the front and back inclined surfaces 86, 90. Still additional embodiments may employ a glue dot on the offset surface 89 instead of or in addition to glue dots being placed on one, the other, or both of the front and back inclined surfaces.

Figure 12:
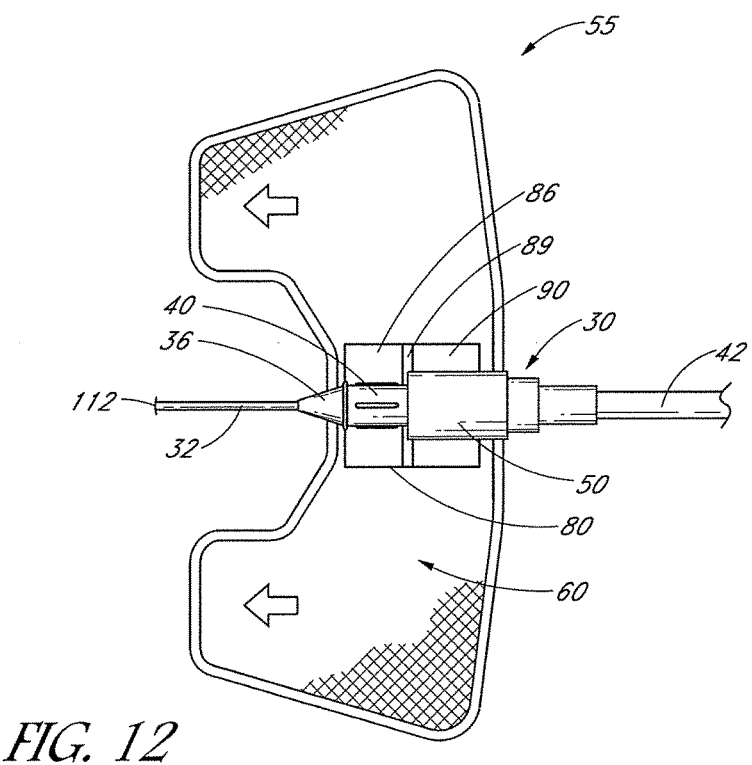
FIG. 12 shows the securement device of FIG. 11 with a catheter assembly attached thereto.

With additional reference to FIG. 12, in use, a clinician removes the release liner from the second inclined surface 90 of the support base 80 to expose the glue dot 100b. The spin nut 50 of the catheter assembly 30 is then placed into contact with the glue dot 100b and the spin nut 50 is pushed into the foam support base 80 in order to help establish a firm adhesive bond. As such, the catheter hub 40 rests upon the front inclined surface 86, but without being directly adhered to the front inclined surface 86. In an additional embodiment, a suture extending through the support pad below the front inclined surface 86 can secure the catheter hub 40 to the front inclined surface without employing an adhesive. As in embodiments described above, a cover, such as an adhesive Tegaderm™ transparent dressing, can be placed over the entire assembly.

A clinician can change a dressing employing the illustrated securement device 55. For example, the Tegaderm™ transparent dressing can be removed and then the spin nut 50 can be pulled off of the support base 80. Preferably the glue dot 100b is configured to preferentially stick to the foam support base 80 so that the glue dot 100b does not stick to the spin nut 50. The spin nut 50 can then be disconnected from the catheter hub 40 so that the associated IV line 42 can be discarded and replaced, while the catheter hub 40 and associated catheter tube 32 can remain in place. Since the hub 40 was never adhered to the support base 80 in this embodiment, there would be no adhesive residue on the surface of the catheter hub 40. The securement device 55 can be peeled off of the patient's skin and replaced with a fresh, sterile securement device 55. A new Luer connector 44 and associated IV line 42 can also be attached to the catheter hub 40. The spin nut 50 of the replacement Luer connector 44 can then be attached via the glue dot 100b to the back inclined surface 90 of the fresh securement device, and a fresh cover dressing 114 can then be placed over the assembly.

Figure 14:
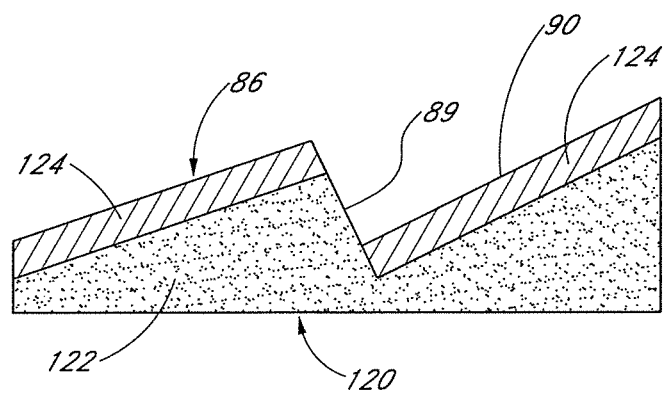
FIG. 14 shows a side view of another embodiment of a support base in accordance with the present disclosure.

With reference next to FIG. 14, another embodiment of a support base 120 is illustrated in which the support base is made up of two different types of materials. For example, the illustrated support base 120 can comprise a first material portion 122 and a second material portion 124. The first and second material portions can comprise different types of foams having for example different levels of malleability, or can comprise entirely different materials. In one preferred embodiment, the first material portion 122 comprises a first foam, and the second material portion 124 can be a gel portion comprising a soft, tacky elastomeric gel or foam. The first foam may be less malleable than the gel, and structurally supports the gel in the second material layer 124. It is to be understood that the second material layer 124 can be used on one, the other or both of the front and back inclined surfaces 86, 90, or on the offset surface 89. In some embodiments the gel may be sufficiently tacky so that no adhesive 100 is deposited on the inclined surface. In other embodiments, however, adhesive is deposited on one or more of the inclined surfaces.

Figure 15:
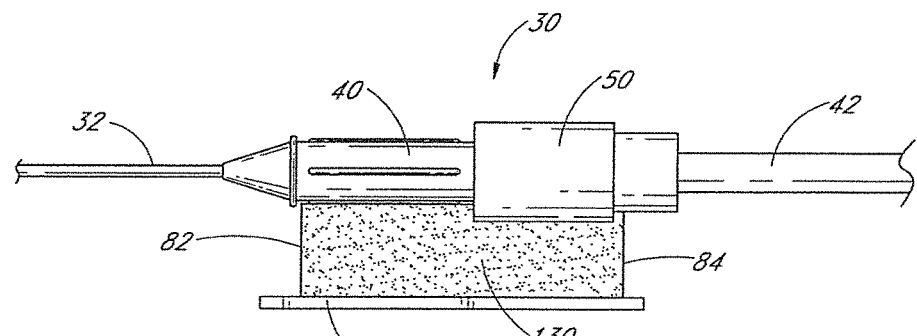
FIG. 15 shows a side view of another embodiment of a securement device having a catheter assembly secured thereon.

In yet additional embodiments, the support base may not have an undulating shape with one, two, or more inclined surfaces. For example, with reference next to FIG. 15, a support base 130 comprises a single, substantially rectangular block of foam. When the catheter assembly 30 is adhered to a flat top surface of the support base 130, the spin nut 50, which has a greater diameter than the catheter hub 40, may crush the foam support base more than the hub 40 does. In another embodiment, the greater diameter of the spin nut 50 will cause the catheter assembly 30 to be held at an incline.

Figure 16:
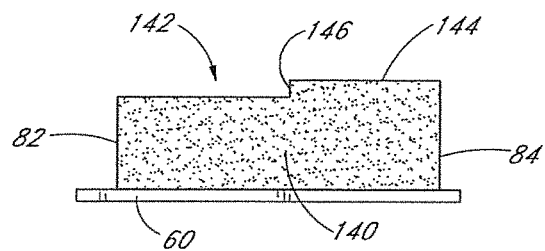
FIG. 16 is a side view of yet another embodiment of a securement device in accordance with the present disclosure.

With reference next to FIG. 16, in another embodiment, a support base 140 is made of a monolithic block of foam having a front portion 142 and a back portion 144. The support base 140 is thicker in the back portion 144 than in the front portion 142, and the front and back portions are connected by an offset 146. Since the back portion 144 is thicker than the front portion 142, a catheter assembly 31 adhered to the support base 140 will be held in an inclined arrangement.

Figure 17:
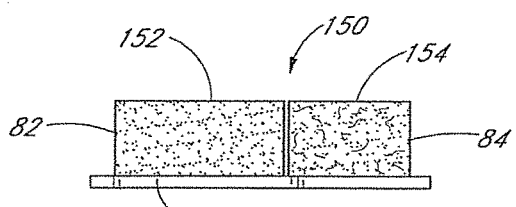
FIG. 17 is a side view of still another embodiment of a securement device in accordance with the present disclosure.
Figure 18:
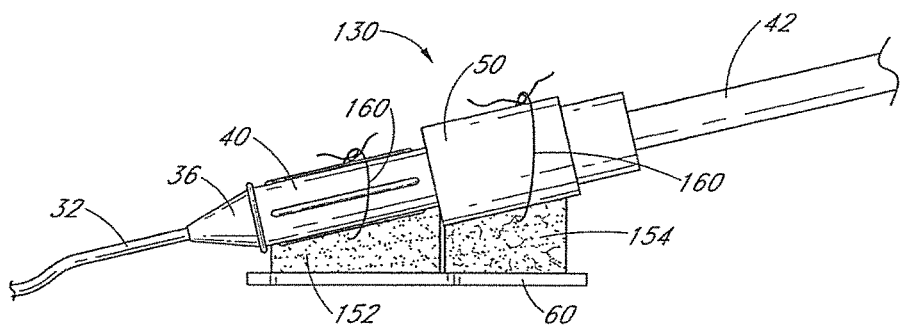
FIG. 18 shows the securement device of FIG. 17 with a catheter assembly secured thereto.

With reference next to FIGS. 17 and 18, in yet another embodiment, a support base 150 can be formed of two separately formed pieces of foam. In the illustrated embodiment, a front part 152 of the support piece base 150 is formed of a first material such as a first foam having a first malleability or softness. The back part 154 of the support base 150 can be formed of a second material such as a second foam having a second softness or malleability. In the illustrated embodiment, the front part 152 is more malleable than the back part 154 so that when the catheter assembly is adhered to the support base 150, the foam beneath the catheter hub 40 crushes more easily than the foam beneath the spin nut 50, and the catheter assembly is supported in an inclined manner. In another embodiment, the back part 154 is more malleable than the front part 152, and thus more easily accepts the increased deformation from the spin nut 50, which has a greater diameter than the hub 40. In all such embodiments, the malleability of the front and back parts can be selected to best support the catheter assembly 30 at a desired angle, whether that angle is generally parallel to the anchor pad 60 or within the range of angles α as discussed above in connection with FIG. 5B.

With continued reference to FIG. 18, another feature is illustrated in which a suture 160 is drawn through the support pad 150 and around the catheter assembly to secure the catheter assembly to the support pad 150. Such a feature can, of course, be combined with any embodiment. The illustrated embodiment shows two sutures 160, but it is to be understood that only one, three, or more can be used as desired. In some embodiments the suture material can be provided through the support pad during manufacturing, and included within a sterile package. In other embodiments a clinician can manually add the suture before or after securing the anchor pad 60 to a patient's skin. Preferably the sutures does not penetrate the patient's skin.

The embodiments described above have employed a catheter assembly with a particular hub design and Luer connector design. It is be understood, however, that embodiments employing the principles discussed above can have somewhat different specific structure in order to accommodate catheters or medical devices with different applications. For example, some catheters that will have somewhat different structure but may still employee principles discussed herein, include central venous catheters, peripherally inserted central catheters, hemodialysis catheters, and Foley catheters. Such other types of catheters may entail different designs and structure for catheter hubs and connectors. Other medical articles having connectors that connect the article to fluid delivery tubes may also employ securement devices exhibiting the principles discussed herein including for example, surgical drainage tubes, feeding tubes, chest tubes, nasogastric tubes, rectal drains, external ventricular drains, chest tubes, or any other sort of medical lines, particularly lines with connector fittings.

The embodiments discussed above have disclosed structures with substantial specificity. This has provided a good context for disclosing and discussing inventive subject matter. However, it is to be understood that other embodiments may employ different specific structural shapes and interactions.

Although inventive subject matter has been disclosed in the context of certain preferred or illustrated embodiments and examples, it will be understood by those skilled in the art that the inventive subject matter extends beyond the specifically disclosed embodiments to other alternative embodiments and/or uses of the invention and obvious modifications and equivalents thereof. In addition, while a number of variations of the disclosed embodiments have been shown and described in detail, other modifications, which are within the scope of the inventive subject matter, will be readily apparent to those of skill in the art based upon this disclosure. It is also contemplated that various combinations or subcombinations of the specific features and aspects of the disclosed embodiments may be made and still fall within the scope of the inventive subject matter. For example, the features concerning materials that can be used in the support base as disclosed in the embodiments depicted in FIGS. 15-18 can also be applied to undulating support base embodiments as in FIGS. 13-14, and vice versa. Accordingly, it should be understood that various features and aspects of the disclosed embodiments can be combined with or substituted for one another in order to form varying modes of the disclosed inventive subject matter. Thus, it is intended that the scope of the inventive subject matter herein disclosed should not be limited by the particular disclosed embodiments described above, but should be determined only by a fair reading of the claims that follow.

What is claimed is:

1. A medical article securement device, comprising:
    an anchor pad configured to be adhered to skin of a patient; and
    a malleable, compressible support base attached to and extending upwardly from the anchor pad, the support base having a first inclined upper surface and a second inclined upper surface that are longitudinally aligned with one another, an offset surface extending between the first and second inclined upper surfaces, the first and second inclined upper surfaces being planar and parallel to one another, the support base further having opposing longitudinally-extending side surfaces extending upwardly from the anchor pad and terminating upon intersecting one of the planar first and second inclined upper surfaces;
    a medical article having a first connector portion having a first diameter and a second connector portion having a second diameter, the second connector portion being positioned adjacent a distal end of the first connector portion, the second diameter being less than the first diameter;
    wherein the first connector portion is supported by the second inclined upper surface and the second connector portion is supported by the first inclined upper surface.

2. A medical article securement device as in claim 1, wherein the first and second connector portions are part of a luer lock connector system, the first connector portion comprising a spin nut, the second connector portion comprising a hub, the first and second connector portions being selectively detachable from one another, and wherein a portion of the distal end of the spin nut engages the offset surface.

3. A medical article securement device as in claim 2 additionally comprising an adhesive layer disposed on a portion of the second inclined upper surface, the first connector being adhered to the second inclined upper surface via the adhesive layer.

4. A medical article securement device as in claim 3 additionally comprising a suture attached to the support pad and wrapped about one of the first and second connector portions.

5. A medical article securement device as in claim 3, wherein the first inclined upper surface does not have an adhesive layer attached thereto.

6. A medical article securement device as in claim 3, wherein the adhesive layer is disposed on only a portion of the second inclined upper surface, and wherein the adhesive layer is generally centered between opposing side edges of the second inclined upper surface, the opposing longitudinally-extending side surfaces intersecting the second inclined upper surface along the opposing side edges.

7. A medical article securement device as in claim 6, wherein the planar second inclined upper surface has a width defined between opposing side edges, and the width is greater than the first diameter.

8. A medical article securement device as in claim 7, wherein the support base comprises a longitudinal axis and the planar first inclined upper surface defines a first plane, and wherein no portion of the support base extends above the first plane.

9. A medical article securement device as in claim 8, wherein the support base comprises a longitudinal axis and the planar second inclined upper surface defines a second plane, and wherein no portion of the support base extends above a line that is defined normal to the longitudinal axis and within the second plane.

10. A medical article securement device as in claim 3, wherein the adhesive layer is configured to preferentially stick to the second inclined upper surface rather than the second connector portion.

11. A medical article securement device as in claim 2, wherein the support base comprises a foam.

12. A medical article securement device as in claim 11, wherein the support base is a monolithic piece of foam.

13. A medical article securement device as in claim 11, wherein the support base comprises a first portion constructed of a first material and a second portion constructed of a second material, and the first material is more malleable than the second material.

14. A medical article securement device as in claim 2, wherein a length of the offset surface approximates the difference between the first diameter and the second diameter.

15. A method, comprising:
providing a medical line system comprising a catheter and a fluid line, the catheter having a hub, the fluid line having a spin nut, the spin nut releasably connected to the catheter hub, a portion of the catheter extending through the skin of a patient;
applying an anchor pad of a securement device onto the skin of the patient, the anchor pad having a support base extending therefrom, the support base having a first inclined surface and a second inclined surface, the first and second inclined surfaces being parallel and joined end to end by an offset surface, the support base further having opposing longitudinally-extending side surfaces extending upwardly from the anchor pad and terminating upon intersecting at least one of the first and second inclined surfaces; and
resting a portion of the medical line system on the support base so that the spin nut is supported upon the second inclined surface and a portion of the catheter hub is supported upon the first inclined surface, and a distal end of the spin nut rests against the offset surface.

16. A method as in claim 15 additionally comprising attaching the spin nut to an adhesive layer arranged on the second inclined surface.

17. A method as in claim 16 additionally comprising detaching the spin nut from the catheter hub.

18. A method as in claim 17 additionally comprising detaching the spin nut from the second inclined surface.

19. A method as in claim 18 additionally comprising discarding the spin nut and fluid line and replacing it with a second fluid line having a second spin nut while the catheter remains in position in the patient, and additionally comprising attaching the second spin nut to the catheter hub and attaching the second spin nut to the second inclined surface.

20. A method as in claim 16, wherein the first and second inclined surfaces are planar and have opposing side edges, the opposing longitudinally-extending side surfaces intersecting the at least one of the first and second inclined surfaces along the opposing side edges, and a width defined between the opposing side edges of the second inclined surface is greater than a diameter of the spin nut.

21. A method as in claim 20, wherein a width of the adhesive layer is no greater than the diameter of the spin nut, and the adhesive layer is placed generally centrally between the opposing side edges of the second inclined surfaces.

22. A method as in claim 20, comprising attaching the spin nut to the second inclined surface before applying the anchor pad onto the skin of the patient.

23. A method as in claim 20, wherein the portion of the catheter hub is supported upon the first inclined surface so that no adhesive on the support base contacts the catheter hub.

24. A method as in claim 23, wherein the spin nut has an axis, and an outer surface of the spin nut extends 360° about the axis, and wherein when the spin nut is supported upon the second inclined surface, more than 180° of the spin nut outer surface is not engaged with the second inclined surface, and additionally comprising adhering an adhesive cover to the patient's skin so that the adhesive cover surrounds more than 180° of the spin nut outer surface.

25. A method as in claim 15, wherein the support base is constructed of a malleable, compressible foam.

* * * * *